United States Patent
Dorn et al.

[11] Patent Number: 6,030,802
[45] Date of Patent: Feb. 29, 2000

[54] LIQUID REAGENT SET FOR L-LACTATE DETERMINATION

[75] Inventors: Allan R. Dorn, Carmel; Catherine J. Hurt, Indianapolis; Larry D. Mountain, Fishers, all of Ind.

[73] Assignee: Roche Diagnostics Corporation, Indianapolis, Ind.

[21] Appl. No.: 09/094,235

[22] Filed: Jun. 9, 1998

Related U.S. Application Data

[63] Continuation-in-part of application No. 09/087,230, May 29, 1998, abandoned.

[51] Int. Cl.[7] .............................. C12Q 1/28; C12Q 1/26; C12Q 1/00
[52] U.S. Cl. ................................ 435/28; 435/25; 435/4; 435/962; 435/963; 435/975; 435/39
[58] Field of Search .................................... 435/28, 25, 4, 435/962, 963, 975, 39

[56] References Cited

U.S. PATENT DOCUMENTS

| | | | |
|---|---|---|---|
| Re. 32,016 | 10/1985 | Esders et al. | 435/28 |
| 4,166,763 | 9/1979 | Esders et al. | 435/28 |
| 4,600,689 | 7/1986 | Matsui et al. | 435/28 |
| 4,910,134 | 3/1990 | Yamanishi et al. | 435/28 |
| 5,108,733 | 4/1992 | Frontini et al. | 435/28 |
| 5,180,672 | 1/1993 | Itoh et al. | 435/28 |
| 5,206,147 | 4/1993 | Hoenes | 435/28 |
| 5,250,420 | 10/1993 | Asano et al. | 435/28 |

FOREIGN PATENT DOCUMENTS

| | | |
|---|---|---|
| 0 411 604 | 2/1995 | European Pat. Off. . |
| 55-138398 | 10/1980 | Japan . |
| 64-002597 | 1/1989 | Japan . |
| 1-171498 | 7/1989 | Japan . |
| 7-278067 | 10/1995 | Japan . |

OTHER PUBLICATIONS

Blake et al.. "A Colorimetric Assay for the Measurement of D–Glucose Consumption by Cultured Cells," *Analytical Biochemistry.* 177:156–160 (1989).

Brandt et al., "Spectrophotometric Assay for D–(–)Lactate in Plasma," *Analytical Biochemistry.* 102:39–46 (1980).

Tamaoku et al., "New Water–Soluble Hydrogen Donors for the Enzymatic Spectrophotometric Determination of Hydrogen Peroxide" *Anal. Chim. Acta.* 136:121–127 (1982).

Tamaoku et al., "New Water–soluble Hydrogen Donors for the Enzymatic Photometric Determination of Hydrogen Peroxide" *Chem. Pharm. Bull.* 30 :(7)2492–2497 (1982).

Theorell, H. and Maehly, A.C., "Untersuchungen an künstlichen Peroxydasen" *Acta Chem. Scand.* 4:422–434 (1950).

Valero et al., "Optimizing Enzymatic Cycling Assays: Spectrophotometric Determination of Low Levles of Pyruvate and L–Lactate, " *Analytical Biochemistry.* 239:47–52 (1996).

White–Stevens, R.H., Interference by Ascorbic Acid in Test Systems Involving Peroxidase.I. Reversible Indicators and the Effects of Copper, Iron, and Mercury. *Clinical Chemistry.* 28(4):578–598 (1982).

*Primary Examiner*—Louise N Leary
*Attorney, Agent, or Firm*—Morrison & Foerster LLP

[57] ABSTRACT

The invention provides sets of liquid reagents that afford calibration stability in an enzyme based spectrophotometric assay for the measurement of lactate in patient samples. The reagent sets include a lactate oxidase, a peroxidase, a hydrogen donor, an agent that substantially prevents ascorbic acid interference, and agent that substantially prevents bilirubin interference, a coupling agent, a buffer and, optionally, a preservative. The invention further provides methods for using the liquid reagent sets.

20 Claims, 1 Drawing Sheet

1

1

LIQUID REAGENT SET FOR L-LACTATE DETERMINATION

This is a continuation-in-part of U.S. application Ser. No. 09/087,230 filed May 29, 1998, (attorney docket number 33746-20034.00) now abandoned, the complete disclosure of which is incorporated herein by reference.

TECHNICAL FIELD

The present invention is directed to sets of liquid reagents that provide calibration stability in an enzyme based spectrophotometric assay for the measurement of lactate in patient samples. The present invention is also directed to a method for using the liquid reagents.

BACKGROUND ART

To diagnose a disease, a physician often looks for the appearance of a chemical marker in a patient. The chemical marker is a specific compound that is expressed in either abnormally high or low amounts during the course of an illness. A clinician examines a patient's plasma and/or cerebrospinal fluid using an assay specifically designed to quantitatively determine the concentration of the marker. A physician observing unusual concentrations of the marker understands that the patient may be suffering from an associated illness.

L-lactate is a chemical marker that is associated with a number of pathological states which result from a reduced oxygenation of biological fluids. Shock, pneumonia and congestive heart failure produce increased levels of L-lactate in plasma. One observes abnormally high cerebrospinal fluid levels of L-lactate as the result of bacterial meningitis, hypocapnia and cerebral ischemia.

Scientists have developed a number of enzymatic assays for the quantitative determination of L-lactate in biological solutions. The most commonly used assay is based on the enzymatic conversion of lactate to pyruvate (Scheme 1). See U.S. Pat. No. 4,166,763. L-lactate is oxidized to pyruvate by lactate oxidase (LOD). The resulting hydrogen peroxide is utilized by peroxidase (POD), which induces the coupling of a hydrogen donor and a coupling agent; a colored dye (chromogen) is formed. The concentration of the chromogen is measured spectrophotometrically. Because the concentration of chromogen is directly proportional to the concentration of lactate in the initial solution, one can calculate an observed lactate concentration.

$$\text{L-lactate} + O_2 \xrightarrow{\text{LOD}} \text{Pyruvate} + H_2O_2 \quad (1)$$

$$H_2O_2 + \text{H donor} + \text{coupling agent} \xrightarrow{\text{POD}} \text{chromogen} + 2H_2O$$

Clinical L-lactate assays are primarily performed by technicians in hospital laboratories. These assays are usually not run as part of a routine panel of tests. Where a patient is suffering from a reduced oxygenation of biological fluids, there is a critical need for an immediate diagnosis. Accordingly, a technician must be able determine L-lactate concentrations as quickly and efficiently as possible.

There are several steps that a technician takes to run an enzyme based, spectrophotometric assay for L-lactate. First a proper wavelength for the spectrophotometric measurement of the chromogen is chosen. Second, a "calibration factor" is established that allows the mathematical conversion of the spectrophotometric measurement of the chromogen to an observed L-lactate concentration. Plasma or cerebrospinal fluid sample from a patient is collected and prepared for testing. Finally, the prepared sample is mixed with the proper enzymatic reagents and there is a spectrophotometric measurement of the absorbence of radiation by the chromogen.

The technician establishes the calibration factor for L-lactate concentration by correlating the original concentration of L-lactate in a sample with the amount of radiation absorbed by the resulting chromogen. To establish this correlation, one has to be able to separate out the absorbence of the chromogen from the absorbence of other components in the assay system. This process can be represented by Scheme 2.

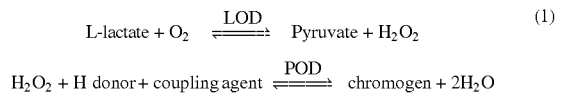

$$\begin{pmatrix}\text{calibration}\\\text{factor}\end{pmatrix} = \begin{pmatrix}\text{absorbence}\\\text{of sample with}\\\text{known L-lactate}\\\text{concentration}\end{pmatrix} \text{minus} \begin{pmatrix}\text{absorbence of}\\\text{sample containing}\\\text{all reagents except}\\\text{L-lactate}\end{pmatrix} \quad (2)$$

The technician combines known concentrations of the assay reagents: lactate oxidase, peroxidase, a hydrogen donor, a coupling agent, and any other chemical element needed to perform the spectrophotometric determination. An aliquot is removed from the reagent combination and absorbence is read on a spectrophotometer. To the stock reagent solution, the technician adds a predetermined amount of L-lactate and allows the enzymatic reactions providing the chromogen to proceed until they are essentially complete. An aliquot of the chromogen containing solution is then removed and a second absorbence reading on the spectrophotometer is taken. The difference between the technician's final and initial spectrophotometric readings is the "calibration factor."

A technician can employ a single set of reagents over an extended period of time; 90 days is not unusual where the technician refrigerates the open containers. Because the reagents are not stable, the calibration factor must be determined frequently during this time period. If one could calculate the calibration factor for a reagent set once, and then use that number for every spectrophotometric assay run with the reagent set, a substantial amount of time in performing an L-lactate assay would be saved. This time savings would allow a physician to more quickly and efficiently interpret the assay results and render a diagnosis.

DISCLOSURE OF THE INVENTION

The use of a calibration factor over an extended period of time requires that the calibration factor remain relatively constant. Accordingly, the components of the reagent set must not chemically react with one another in the given time frame to afford products that absorb radiation at the same wavelength as the chromogen.

A set of assay reagents can be either in a solid phase cartridge form or in a liquid form. Solid phase cartridges are limited to use in specialized instruments designed to receive the cartridges. Liquid reagents, on the other hand, can be used in a variety of generalized instruments. This versatility allows hospital laboratories to maintain fewer instruments and therefore reduces the costs associated with laboratory testing. Furthermore, where a reagent is in liquid form, the user does not need to reconstitute it prior to performing the assay. A technician can more quickly determine the L-lactate concentration in a biological fluid and also eliminate mixing errors associated with the reagent reconstitution.

The development of a liquid reagent set for an L-lactate assay that exhibits a relatively constant calibration factor, therefore, meets an important need. It provides for a more efficient diagnosis of a set of critical medical conditions. The present invention provides a liquid reagent set for an L-lactate spectrophotometric assay.

In one embodiment, the liquid reagent set includes a lactate oxidase, a peroxidase, a hydrogen donor of structure 1, an agent that substantially prevents

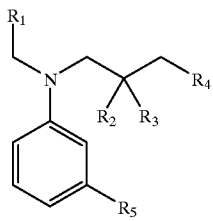

1 ascorbic acid interference, an agent that substantially prevents bilirubin interference, a coupling agent and a buffer. The substituents on hydrogen donor 1 are defined as follows: $R_1$ is hydrogen or alkyl; $R_2$ and $R_3$ are, independently, hydrogen, alkyl or aryl; $R_4$ is $SO_3M$ or $CO_2M$, wherein M is hydrogen or a cation; and $R_5$ is hydrogen or alkyl. In this embodiment, the reagent set exhibits a calibration factor that varies by less than about 10% over a period of about 20 days, when the reagent set is stored at 4° C.

In another embodiment, the lactate oxidase is isolated from a microorganism.

In another embodiment, the peroxidase is isolated from horseradish.

In another embodiment, the substituents of the hydrogen donor are defined as follows: $R_1$ is alkyl; $R_2$ and $R_3$ are hydrogen; $R_4$ is $SO_3M$, wherein M is a cation; and $R_5$ is alkyl.

In another embodiment, the agent that substantially prevents ascorbic acid interference is a biological oxidizing agent.

In another embodiment, the agent that substantially prevents bilirubin interference is a chemical oxidizing agent.

In another embodiment, the coupling agent is 4-aminoantipyrine or a 4-aminoantipyrine analogue.

In another embodiment, the buffer is a phosphate buffer.

In another embodiment, the reagent set exhibits a calibration factor that varies by less than about 7% over a period of about 40 days.

In another embodiment, the reagent set further comprises a preservative.

In another embodiment, the reagent set exhibits a calibration factor that varies by less than about 7% over a period of about 40 days, and the substituents of the hydrogen donor are defined as follows: $R_1$ is methyl; $R_2$ and $R_3$ are hydrogen; $R_4$ is $SO_3M$, wherein M is sodium; and $R_5$ is methyl.

In another embodiment, the reagent set further comprises a preservative, and the preservative is sodium azide.

In another embodiment, the reagent set further comprises a preservative, and the preservative is sodium azide. In this embodiment, the substituents of the hydrogen donor are defined as follows: $R_1$ is methyl; $R_2$ and $R_3$ are hydrogen; $R_4$ is $SO_3M$, wherein M is sodium; and $R_5$ is methyl.

In another embodiment, the reagent set further comprises a preservative, and the preservative is sodium azide. In this embodiment, the buffer is a phosphate buffer, and the substituents of the hydrogen donor are defined as follows: $R_1$ is methyl; $R_2$ and $R_3$ are hydrogen; $R_4$ is $SO_3M$, wherein M is sodium; and $R_5$ is methyl.

In another embodiment, the reagent set further comprises a preservative, and the preservative is sodium azide. In this embodiment, the buffer is a phosphate buffer, and the substituents of the hydrogen donor are defined as follows: $R_1$ is methyl; $R_2$ and $R_3$ are hydrogen; $R_4$ is $SO_3M$, wherein M is sodium; and $R_5$ is methyl. This reagent set exhibits a calibration factor that varies by less than about 7% over a period of about 40 days.

In another embodiment, the reagent set further comprises a preservative, and the preservative is sodium azide. In this embodiment, the buffer is a phosphate buffer, and the substituents of the hydrogen donor are defined as follows: $R_1$ is methyl; $R_2$ and $R_3$ are hydrogen; $R_4$ is $SO_3M$, wherein M is sodium; and $R_5$ is methyl. This reagent set exhibits a calibration factor that varies by less than about 5% over a period of about 60 days.

The present invention also provides a method for determining the concentration of L-lactate in a biological fluid.

In one embodiment, the method includes the following steps: collecting a biological fluid from a subject; and, performing a spectrophotometric assay on the biological fluid using a liquid reagent set. The liquid reagent set in this embodiment includes a lactate oxidase, a peroxidase, a hydrogen donor of structure 1, an agent that substantially prevents ascorbic acid interference, an

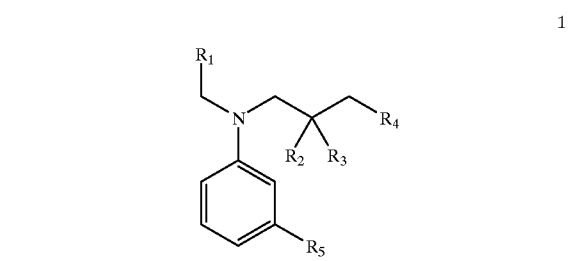

1 agent that substantially prevents bilirubin interference, a coupling agent and a buffer. The substituents on hydrogen donor 1 are defined as follows: $R_1$ is hydrogen or alkyl; $R_2$ and $R_3$ are, independently, hydrogen, alkyl or aryl; $R_4$ is $SO_3M$ or $CO_2M$, wherein M is hydrogen or a cation; and $R_5$ is hydrogen or alkyl. The reagent set exhibits a calibration factor that varies by less than about 10% over a period of about 20 days, when the reagent set is stored at 4° C.

In another embodiment, the substituents of the hydrogen donor of the liquid reagent set used in the L-lactate determination method are defined as follows: $R_1$ is methyl; $R_2$ and $R_3$ are hydrogen; $R_4$ is $SO_3M$, wherein M is a sodium ion; and $R_5$ is methyl.

The present invention also provides a method for determining the concentration of L-lactate in a biological fluid, wherein a reagent set used in the determination includes a preservative.

In one embodiment, the method includes the following steps: collecting a biological fluid from a subject; and, performing a spectrophotometric assay on the biological fluid using a liquid reagent set. The liquid reagent set in this embodiment includes a lactate oxidase, a peroxidase, a hydrogen donor of structure 1, an agent that substantially prevents ascorbic acid interference, an

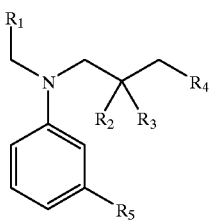

agent that substantially prevents bilirubin interference, a coupling agent, a buffer, and a preservative. The substituents on hydrogen donor 1 are defined as follows: $R_1$ is hydrogen or alkyl; $R_2$ and $R_3$ are, independently, hydrogen, alkyl or aryl; $R_4$ is $SO_3M$ or $CO_2M$, wherein M is hydrogen or a cation; and $R_5$ is hydrogen or alkyl. The reagent set exhibits a calibration factor that varies by less than about 10% over a period of about 20 days, when the reagent set is stored at 4° C.

In another embodiment, the substituents of the hydrogen donor of the liquid reagent set used in the L-lactate determination method are defined as follows: $R_1$ is methyl; $R_2$ and $R_3$ are hydrogen; $R_4$ is $SO_3M$, wherein M is a sodium ion; and $R_5$ is methyl.

BEST MODE FOR CARRYING OUT THE INVENTION

Definitions

Figure 1:
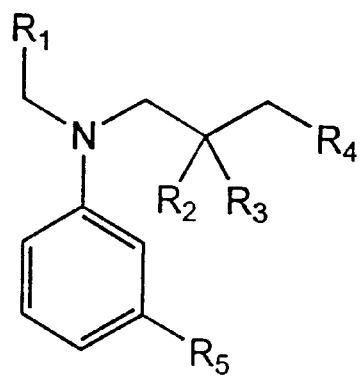
FIG. 1 shows a general structure for a hydrogen donor of the present invention.

"Biological fluid" refers to any liquid substance removed from a living organism. Preferably, the biological fluid will be either plasma or cerebrospinal fluid. More preferably, the biological fluid will be either plasma or cerebrospinal fluid from a human. "Calibration factor" is a number that allows one to mathematically convert the spectrophotometric measurement of a chromogen to an observed L-lactate concentration. One obtains this number by correlating a known concentration of L-lactate in a sample with the amount of UV radiation absorbed by the chromogen which is produced from the reaction of L-lactate. This process is illustrated in Scheme 2.

"Hydrogen donor" refers to a compound that is oxidized in a chemical reaction, resulting in the formation of a chromogen in a spectrophotometric assay. Hydrogen donors are known within the art, and examples of hydrogen donors include, but are not limited to, the following compounds: phenol, 4-chlorophenol, 2,4-dichlorophenol-6-sulphonic acid, N,N-dialkylaniline, N,N-dialkyl-m-toluidine, sodium salt of N-ethyl-N-sulphopropylaniline, sodium salt of N-ethyl-N-sulphopropyl-m-toluidine, sodium salt of N-ethyl-N-sulphopropyl-m-anisidine, sodium salt of N-ethyl-N-(2-hydroxy-3-sulfopropyl)-m-toluidine, sodium salt of N-ethyl-N-(2-hydroxy-3-sulfopropy)-m-anisidine, sodium salt of 3,5-dimethyl-N-ethyl-N-(2-hydroxy-3-sulfopropyl)aniline and sodium salt of 3,5-dimethoxy-N-ethyl-N-(2-hydroxy-3-sulfopropyl)aniline.

"Coupling agent" refers to a compound that couples to an oxidized hydrogen donor, resulting in the formation of a chromogen in a spectrophotometric assay. Coupling agents are known within the art, and examples of coupling agents include, but are not limited to, the following compounds: 4-aminoantipyrine; trisubstituted 4-amino-3-pyrazoline-5-ones, such as 1-(2,4,6-trichlorophenyl)-2,3-dimethyl-4-amino-pyrazoline-5-one and 1-(3,5-dichlorophenyl)-2,3-dimethyl-4-amino-3-pyrazoline-5-one; and, 4-aminoantipyrine analogues, such as 1-phenyl-2,3-dimethyl-4-dimethylamino-3-pyrazoline-5-one. Preferably, the coupling agent is 4-aminoantipyrine or a 4-aminoantipyrine analogue. More preferably, the coupling agent is 4-aminoantipyrine.

"Substantially stable calibration factor" refers to a calibration factor that does not vary by more than about 10% over a period of about 20 days. Preferably, the calibration factor does not vary by more than about 7% over a period of about 20 days. More preferably, the calibration factor does not vary by more than about 7% over a period of about 40 days. Still more preferably, the calibration factor does not vary by more than 5% over a period of about 40 days. Most preferably, the calibration factor does not vary by more than about 5% over a period of 60 days.

"Agent that substantially prevents ascorbic acid interference" refers to a chemical or biological oxidizing compound. Ascorbic acid interference results from the conversion of ascorbic acid to ascorbate, which acts to reduce a chromogen in a spectrophotometric assay. The chemical or biological agent oxidizes at least 90% of the ascorbate to ascorbic acid in a sample, thereby substantially preventing the interference. Preferably, the agent oxidizes at least 95% of the ascorbate to ascorbic acid. More preferably, the agent oxidizes at least 99% of the ascorbate to ascorbic acid.

"Agent that substantially prevents bilirubin interference" refers to a chemical or biological oxidizing compound. Bilirubin interference results because bilirubin absorbs light at wavelengths commonly used for spectrophotometric assays. The chemical or biological agent oxidizes at least 90% of the bilirubin in a sample, thereby substantially preventing the interference. Preferably, the agent oxidizes at least 95% of the bilirubin. More preferably, the agent oxidizes at least 99% of the bilirubin.

Enzyme Based Spectrophotometric L-Lactate Assay

The present invention is directed to sets of liquid reagents that provide calibration stability in an enzyme based spectrophotometric assay for the measurement of lactate in patient samples. The reagent sets for the spectrophotometric assay include a lactate oxidase, a peroxidase, a hydrogen donor, an agent that substantially prevents ascorbic acid interference, an agent that substantially prevents bilirubin interference, a coupling agent, a buffer and, optionally, a preservative.

One of ordinary skill in the art will understand that any lactate oxidase that is suitable for the spectrophotometric assay can be used. The lactate oxidase should be specific for L-lactate, soluble, catalase free and highly stable. A nonlimiting example of a lactate oxidase that meets those criteria is produced by Streptococcus faecalis. See U.S. Pat. No. 4,166,763. Preferably, the lactate oxidase used in the present invention is isolated from a microorganism.

The lactate oxidase is present in the reagent set at a concentration ranging from about 2.6 U/mL to about 17.5 U/mL. Preferably, the lactate oxidase is present at a concentration ranging from about 10.0 U/mL to about 17.5 U/mL. More preferably, the lactate oxidase is present at a concentration ranging from about 12.5 U/mL to about 17.5 U/mL. Most preferably, the lactate oxidase is present at a concentration of about 15.0 U/mL.

The peroxidase used in the present invention can be isolated from a variety of sources. A nonlimiting list of peroxidase sources includes horseradish, potatoes, figtree sap, turnips (plant peroxidase), milk (lacto peroxidase), white blood corpuscles (verdo peroxidase) and microorganisms. See U.S. Pat. No. 4,166,763. Certain synthetic peroxidases are also suitable for use in the present invention. See Theorell et al. (1950) *Acta Chem. Scand.* 4:422–433. Preferably, the peroxidase is isolated from horseradish.

The peroxidase is present in the reagent set at a concentration ranging from about 2.0 U/mL to about 30.0 U/mL. Preferably, the peroxidase is present at a concentration ranging from about 10 U/mL to about 30.0 U/mL. More preferably, the peroxidase is present at a concentration ranging from about 20 U/mL to about 30.0 U/mL. Most preferably, the peroxidase is present at a concentration of about 24 U/mL.

The hydrogen donor used in the present invention is an aniline derivative of the following structure:

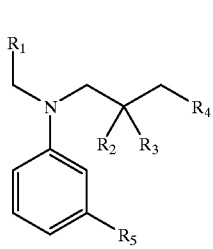

1 wherein $R_1$ is hydrogen or alkyl; $R_2$ and $R_3$ are, independently, hydrogen, alkyl or aryl; $R_4$ is $SO_3M$ or $CO_2M$, wherein M is hydrogen or a cation; and $R_5$ is hydrogen or alkyl. Preferably, $R_1$ is alkyl, $R_2$ and $R_3$ are hydrogen; $R_4$ is $SO_3M$; and $R_5$ is alkyl. More preferably, $R_1$ is methyl, ethyl or propyl; $R_2$ and $R_3$ are hydrogen; $R_4$ is $SO_3Na$; and $R_5$ is methyl, ethyl or propyl. Most preferably, $R_1$ is methyl; $R_2$ and $R_3$ are hydrogen; $R_4$ is $SO_3Na$; and $R_5$ is methyl (sodium salt of N-ethyl-N-sulfopropyl-m-toluidine). (For syntheses of such compounds, see Tamaoku et al. (1982) *Anal. Chim. Acta* 136:121–127 and Tamaoku et al. (1982) *Chem. Pharm. Bull* 30:2492–2497.)

A hydrogen donor used in the present invention will not chemically react with itself or other components in the reagent set to afford a substantial amount of a chromogenic product at about 4° C. One can select a hydrogen donor for use in the present invention, for example, by measuring the absorbence of a particular reagent set, which is stored at about 4° C. over an extended period of time. For instance, at day 0 aliquots from reagents A and B are mixed. After standing for 143–190 seconds the sample absorbence is measured at 660 nm.

TABLE 1

Reagent Set A and B

| A | B |
|---|---|
| $NaH_2PO_4 \times H_2O$ 7.7 mM | $CaCl_2 \times 2\ H_2O$ 0.008 mM |
| $Na_2HPO_4 \times 2\ H_2O$ 94.5 mM | $NaH_2PO_4 \times H_2O$ 7.7 mM |
| $NaN_3$ 14.6 mM | $Na_2HPO_4 \times 2\ H_2O$ 94.5 mM |
| Hydrogen Donor 3.5 mM | $NaN_3$ 14.6 mM |
| ascorbate oxidase 30 kU/L | $K_4[Fe(CN)_6] \times 3\ H_2O$ 0.3 mM |
| pH 7.80 | 4-AAP 5 mM |
| | lactate oxidase 15 kU/L |
| | peroxidase 24 kU/L |
| | pH 7.80 |

At days 7, 14 and 21 the procedure is repeated. Where the absorbence value at day 21 is more than about 10% different from the absorbence value at day 0, the reagent set does not provide for a relatively stable calibration factor; the hydrogen donor included in the reagent set should not be selected.

This process can be further illustrated through the use of a sample calculation. Hydrogen donor X is included in a reagent set. At day 0, the reagent set provides an absorbence reading of 100. The absorbence readings for the reagent set at days 7, 14 and 21 are respectively, 104, 109 and 114. Between day 21 and day 0 there has been a 14% variation in the absorbence reading: (114−100)/100=14%. Hydrogen donor X should not be selected for use in the present invention.

The hydrogen donor is present in the reagent set at a concentration ranging from about 0.48 g/L (1.75 mM) to about 1.92 g/L (7 mM). Preferably, the hydrogen donor is present at a concentration ranging from about 0.75 g/L to about 1.5 g/L. More preferably, the hydrogen donor is present at a concentration ranging from about 0.85 g/L to about 1.25 g/L. Most preferably, the hydrogen donor is present at a concentration of about 0.98 g/L.

The agent that substantially prevents ascorbic acid interference is either a chemical or biological oxidizing agent. Chemical oxidizing agents that prevent ascorbic acid interference include, without limitation, Fe(III)-HEDTA and iodate. Ascorbate oxidase is an example of a biological oxidizing agent that is used in the present invention. Preferably, the agent is a biological oxidizing agent. More preferably, it is ascorbate oxidase.

The agent that substantially prevents ascorbic acid interference is present in the reagent set at a concentration ranging from about 26.0 U/mL to about 34.0 U/mL. Preferably, the agent is present at a concentration ranging from about 28.0 U/mL to about 32 U/mL. More preferably, the agent is present at a concentration ranging from about 29.0 U/mL to about 31.0 U/mL. Most preferably, the agent is present at a concentration of about 30.0 U/mL.

The agent that substantially prevents bilirubin interference is either a chemical or biological oxidizing agent. Bilirubin oxidase is an example of a biological oxidizing agent that is used in the present invention. Chemical oxidizing agents that prevent bilirubin interference include, without limitation, potassium ferrocyanide, sodium ferrocyanide, calcium ferrocyanide, ammonium ferrocyanide and compounds that are capable of generating ferrocyanide. Preferably, the agent is a chemical oxidizing agent. More preferably, it is potassium ferrocyanide ($K_4[Fe(CN)_6]$).

The agent that substantially prevents bilirubin interference is present in the reagent set at a concentration ranging from about 0.08 g/L to about 0.2 g/L. Preferably, the agent is present at a concentration ranging from about 0.09 g/L to about 0.15 g/L. More preferably, the agent is present at a concentration ranging from about 0.1 g/L to about 0.14 g/L. Most preferably, the agent is present at a concentration of about 0.13 g/L.

The coupling agent is a compound that couples with an oxidized hydrogen donor to provide a chromogen. Examples of coupling agents include, but are not limited to, the following compounds: 4-aminoantipyrine; trisubstituted 4-amino-3-pyrazoline-5-ones, such as 1-(2,4,6-trichlorophenyl)-2,3-dimethyl-4-amino-pyrazoline-5-one and 1-(3,5-dichlorophenyl)-2,3-dimethyl-4-amino-3-pyrazoline-5-one; and, 4-aminoantipyrine analogues, such as 1-phenyl-2,3-dimethyl4-dimethylamino-3-pyrazoline-5-one. Preferably, the coupling agent is 4-aminoantipyrine or a 4-aminoantipyrine analogue. More preferably, the coupling agent is 4-aminoantipyrine.

The coupling agent is present in the reagent set at a concentration ranging from about 1.0 mM to about 7.0 mM. Preferably, the coupling agent is present at a concentration ranging from about 2.0 mM to about 6.0 mM. More preferably, the coupling agent is present at a concentration ranging from about 2.5 mM to about 5.5 mM. Most preferably, the coupling agent is present at a concentration of about 2.9 mM.

The buffer is of a suitable buffering capacity to maintain a pH range of about 6.0 to about 7.9 in the reagent set. Preferably, the buffer system maintains a pH range of about 7.0 to about 7.9. More preferably, the buffer system maintains a pH range of about 7.5 to about 7.9. Most preferably, the buffer system maintains a pH range of about 7.7 to 7.9.

Nonlimiting examples of a buffer include phosphate, HEPES, 4-morpholine propanesulfonic acid (MOPS), 2-[tris(hydroxymethyl)methylamino]-1-ethane-sulfonic acid (TES), and TRIS. Preferably, the buffer is a phosphate buffer.

The reagent sets of the present invention optionally contain a preservative. Nonlimiting examples of preservatives include sodium azide, hydroxybenzoic acid, gentarnicin, Thymol and mercury-free preservatives. Preferably, the preservative is sodium azide.

The preservative, when it is in the reagent set, is present at a concentration ranging from about 0.05% to about 0.4%. Preferably, the preservative is present at a concentration ranging from about 0.075% to about 0.3%. More preferably, the preservative is present at a concentration ranging from about 0.085% to about 0.25%. Most preferably, the preservative is present at a concentration ranging from about 0.09% to about 0.2%.

A reagent set of the present invention that does not contain a preservative in the presence of a hydrogen donor, when stored at a temperature of about 35° C., will provide for a calibration factor that varies by less than about 10% over a period of about 20 days. Preferably, the reagent set will provide for a calibration factor that varies by less than about 10% over a period of about 40 days. More preferably, the reagent set will provide for a calibration factor that varies by less than about 7% over a period of about 40 days.

A reagent set of the present invention that does contain a preservative in the presence of a hydrogen donor, when stored at a temperature of about 4° C., will provide for a calibration factor that varies by less than about 10% over a period of about 20 days. Preferably, the reagent set will provide for a calibration factor that varies by less than about 7% over a period of about 20 days. More preferably, the reagent set will provide for a calibration factor that varies by less than about 7% over a period of about 40 days. Still more preferably, the reagent set will provide for a calibration factor that varies by less than about 5% over a period of about 40 days. Most preferably, the reagent set will provide for a calibration factor that varies by less than 5% over a period of about 60 days.

PREFERRED EMBODIMENTS

The reagent set consisting essentially of compositions R1 and R2 is a preferred embodiment of the present invention. Reagent R1 contains $NaH_2PO_4 \times H_2O$, $Na_2HPO_4 \times 2H_2O$, sodium azide, ascorbate oxidase and N-ethyl-N-sulfopropyl-m-toluidine, sodium salt as the hydrogen donor. Reagent R2 contains $CaCl_2 \times 2H_2O$, $NaH_2PO_4 \times H_2O$, $Na_2HPO_4 \times 2H_2O$, sodium azide, $K_4[Fe(CN)_6] \times 3H_2O$, 4-AAP, lactate oxidase and peroxidase.

TABLE 2

Composition of Reagent Set R1 and R2

| R1 | R2 |
|---|---|
| $NaH_2PO_4 \times H_2O$ 7.7 mM | $CaCl_2 \times 2 H_2O$ 0.008 mM |
| $Na_2HPO_4 \times 2 H_2O$ 94.5 mM | $NaH_2PO_4 \times H_2O$ 7.7 mM |
| $NaN_3$ 14.6 mM | $Na_2HPO_4 \times 2 H_2O$ 94.5 mM |
| TOPS 3.5 mM | $NaN_3$ 14.6 mM |
| ascorbate oxidase 30 kU/L | $K_4[Fe(CN)_6] \times 3 H_2O$ 0.3 mM |
| pH 7.80 | 4-AAP 5 mM |
|  | lactate oxidase 15 kU/L |
|  | peroxidase 24 kU/L |
|  | pH 7.80 |

Reagent set R1 and R2 provides calibration stability in an enzyme based spectrophotometric assay for the measurement of lactate. The absorbence of the reagent set at 660 nm was measured at days 0, 7, 14 and 21. At day 0, the absorbence was 86. At days 7, 14 and 21 the absorbence was, respectively, 83, 83 and 83. Between days 21 and 0, therefore, there was a variation in absorbence of approximately only 3.5%: (86−83)/86.

This result should be contrasted with a similar reagent set, where the hydrogen donor N-ethyl-N-sulfopropyl-m-toluidine, sodium salt was replaced with N-ethyl-N-(2-hydroxy-3-sulfopropyl)-m-toluidine, sodium salt. As with the previous reagent set, the absorbence was measured at days 0, 7, 14 and 21. The absorbence for those days was, respectively, 59, 105, 131 and 155. There was a variation in absorbence of approximately 163% between days 21 and 0: (155−59)/59.

In another preferred embodiment, the reagent set consists essentially of reagents R3 and R4. Reagent R3 contains $NaH_2PO_4 \times H_2O$, $Na_2HPO_4 \times 2H_2O$, ascorbate oxidase and N-ethyl-N-sulfopropyl-m-toluidine, sodium salt as the hydrogen donor. Reagent R4 contains $CaCl_2 \times 2H_2O$, $NaH_2PO_4 \times H_2O$, $Na_2HPO_4 \times 2H_2O$, sodium azide, $K_4[Fe(CN)_6] \times 3H_2O$, 4-AAP, lactate oxidase and peroxidase.

TABLE 3

Composition of Reagent Set R3 and R4

| R3 | R4 |
|---|---|
| $NaH_2PO_4 \times H_2O$ 7.7 mM | $CaCl_2 \times 2 H_2O$ 0.008 mM |
| $Na_2HPO_4 \times 2 H_2O$ 94.5 mM | $NaH_2PO_4 \times H_2O$ 7.7 mM |
| TOPS 3.5 mM | $Na_2HPO_4 \times 2 H_2O$ 94.5 mM |
| ascorbate oxidase 30 kU/L | $NaN_3$ 14.6 mM |
| pH 7.80 | $K_4[Fe(CN)_6] \times 3 H_2O$ 0.3 mM |
|  | 4-AAP 5 mM |
|  | lactate oxidase 15 kU/L |
|  | peroxidase 24 kU/L |
|  | pH 7.80 |

Reagent set R3 and R4 also provides calibration stability in an enzyme based spectrophotometric assay for the measurement of lactate. The absorbence of the reagent set R3 and R4 at 660 nm was measured over a period of 48 days at 35° C. and compared to the absorbence of reagent set R1 and R2 under the same conditions. Reagent set R1 and R2 exhibited a variation of approximately 23% over a 48 day period; reagent set R3 and R4 is exhibited a variation of approximately 7% over a 48 day period.

Biological Fluid Collection and Preparation

One of ordinary skill in the art will understand that any method of biological fluid collection and preparation can be used to provide a sample for an L-lactate assay. For example, plasma from blood collected in fluoride-oxalate tubes (2.5 mg sodium fluoride and 2.0 mg potassium oxalate/mL blood) by a standard venipuncture technique can serve as a suitable biological fluid sample. Serum should not be used to provide the sample. Cerebrospinal fluid obtained according to standard methods known in the art can be used.

The person drawing a biological fluid sample should realize that lactate levels increase rapidly with physical exercise. The time required for lactate values to return to normal depends on the physical fitness of the subject. A resting period of thirty minutes, however, is sufficient for the typical patient.

Where the biological fluid specimen is from blood, the blood sample should be drawn from a stasis-free vein. Minimal hemostasis—less than 30 seconds—though, will not affect lactate levels. The person drawing the blood should avoid using a tourniquet if possible.

The stability of the biological sample varies according to its source. Lactate is stable in separated plasma for 2 days at 2–8° C. or 2 hours at 20–25° C. Lactate in CSF is stable for 24 hours at 2–8° C., 3 hours at 20–25° C. or 1 month at −20° C.

EXAMPLES

Abbreviations

LOD, lactate oxidase; POD, peroxidase; 4-AAP, 4-aminoantipyrine; $H_2O_2$, hydrogen peroxide; TOPS, N-ethyl-N-sulfopropyl-m-toluidine; TOOS, N-ethyl-N-(2-hydroxy-3-sulfopropyl)-m-toluidine; $NaN_3$, sodium azide.

General

Lactate measurements were performed using a Boehringer Mannheim/Hitachi 717 Analyzer. The primary wavelength used for spectrophotometric analysis was 660 nm. The secondary wavelength used for spectrophotometric analysis was 700 nm. The following reagents were obtained from Boehringer Mannheim GmbH: lactate oxidase (ID number 1 798 197); peroxidase (catalog number 012 1606 102); $K_4[Fe(CN)_6] \times 3H_2O$ (ID number 0 034 592 001); ascorbate oxidase (catalog number 0199 605 102); and phosphate buffer (ID number 0 004 537). Sodium azide was purchased from Fairmont Chemical Company (catalog number 4565). N-Ethyl-N-sulfopropyl-m-toluidine, sodium salt was purchased from Research Organics (catalog number 3026 E). Other hydrogen donors are synthesized according to the methods disclosed in Tamaoku et al. (1982) *Anal. Chim. Acta* 136:121–127 and Tamaoku et al. (1982) *Chem. Pharm. Bull.* 30:2492–2497.

Procedure for Lactate Measurement Using Reagent R1 and R2

A biological fluid sample (3 μL) was dispensed into a 37° C. cuvette (water bath controlled) by a Boehringer Mannheim/Hitachi 717 Analyzer. Reagent R1 (Table 1, 250 μL) was added and mixed with the biological sample. After a 5 minute incubation, reagent R2 (Table 1, 50 μL) was added and mixed. The cuvette was allowed to stand for 140–193 seconds. The sample absorbence was measured at 660 nm.

Preparation of 1 Liter of R1 Reagent

Approximately 800 mL of deionized, high purity water was dispensed into a polypropylene container. $NaH_2PO_4 \times H_2O$ (1.06 g) and $Na_2HPO_4 \times 2H_2O$ (16.82 g) were dissolved in the deionized water. $NaN_3$ (0.95 g), TOPS (0.98 g) and 30,000 units of ascorbate oxidase were then added to the solution and dissolved. The solution was stirred and the volume adjusted to 1.0 liter with deionized, high purity water. The R1 reagent was stored at 2–8° C.

Preparation of 1 Liter of R2 Reagent

Approximately 800 mL of deionized, high purity water was dispensed into a polypropylene container. $CaCl_2 \times 2H_2O$ (1.17 mg), $NaH_2PO_4 \times H_2O$ (1.06 g) and $Na_2HPO_4 \times 2H_2O$ (16.82 g) were dissolved in the deionized water. $NaN_3$ (0.95 g), $K_4[Fe(CN)_6] \times 3H_2O$ (0.127 g) and 4-AAP (1.016 g) were added to the solution and dissolved. LOD (15,000 units) was carefully added and dissolved. POD (24,000 units) was carefully added and dissolved. The solution volume was adjusted to 1.0 liter with deionized, high purity water. The R2 reagent was stored at 2–8° C.

Procedure for Lactate Measurement Using Reagent Set R3 and R4.

A biological fluid sample (3 μL) was dispensed into a 37° C. cuvette (water bath controlled) by a Boehringer Mannheim/Hitachi 717 Analyzer. Reagent R3 (Table 1, 250 μL) was added and mixed with the biological sample. After a 5 minute incubation, reagent R4 (Table 1, 50 μL) was added and mixed. The cuvette was allowed to stand for 140–193 seconds. The sample absorbence was measured at 660 nm.

Preparation of 1 Liter of R3 Reagent

Approximately 800 mL of deionized, high purity water was dispensed into a polypropylene container. $NaH_2PO_4 \times H_2O$ (1.06 g) and $Na_2HPO_4 \times 2H_2O$ (16.82 g) were dissolved in the deionized water. TOPS (0.98 g) and 30,000 units of ascorbate oxidase were then added to the solution and dissolved. The solution was stirred and the volume adjusted to 1.0 liter with deionized, high purity water. The R3 reagent was stored at 2–8° C.

Preparation of 1 Liter of R4 Reagent

Approximately 800 mL of deionized, high purity water was dispensed into a polypropylene container. $CaCl_2 \times 2H_2O$ (1.17 mg), $NaH_2PO_4 \times H_2O$ (1.06 g) and $Na_2HPO_4 \times 2H_2O$ (16.82 g) were dissolved in the deionized water. $NaN_3$ (0.95 g), $K_4[Fe(CN)_6] \times 3H_2O$ (0.127 g) and 4-AAP (1.016 g) were added to the solution and dissolved. LOD (15,000 units) was carefully added and dissolved. POD (24,000 units) was carefully added and dissolved. The solution volume was adjusted to 1.0 liter with deionized, high purity water. The R4 reagent was stored at 2–8° C.

We claim:

1. A liquid reagent set for an L-lactate spectrophotometric assay, wherein the reagent set comprises:

a) a lactate oxidase;

b) aperoxidase;

c) a hydrogen donor of structure 1

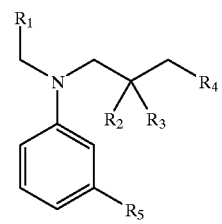

1 wherein $R_1$ is hydrogen or alkyl; $R_2$ and $R_3$ are, independently, hydrogen, alkyl or aryl; $R_4$ is $SO_3M$ or $CO_2M$, wherein M is hydrogen or a cation; and $R_5$ is hydrogen or alkyl;

d) an agent that substantially prevents ascorbic acid interference;

e) an agent that substantially prevents bilirubin interference;

f) a coupling agent; and g) a buffer;

wherein the reagent set exhibits a calibration factor that varies by less than about 10% over a period of about 20 days, when the reagent set is stored at about 4° C.

2. The liquid reagent set according to claim 1, wherein the lactate oxidase is isolated from a microorganism.

3. The liquid reagent set according to claim 1, wherein the peroxidase is isolated from horseradish.

4. The liquid reagent set according to claim 1, wherein the substituents of the hydrogen donor are as follows: $R_1$ is alkyl; $R_2$ and $R_3$ are hydrogen; $R_4$ is $SO_3M$, wherein M is a cation; and $R_5$ is alkyl.

5. The liquid reagent set according to claim 1, wherein the agent that substantially prevents ascorbic acid interference is a biological oxidizing agent.

6. The liquid reagent set according to claim 1, wherein the agent that substantially prevents bilirubin interference is a chemical oxidizing agent.

7. The liquid reagent set according to claim 1, wherein the coupling agent is 4-aminoantipyrine or a 4-aminoantipyrine analogue.

8. The liquid reagent set according to claim 1, wherein the buffer is a phosphate buffer.

9. The liquid reagent set according to claim 1, wherein the reagent set exhibits a calibration factor that varies by less than about 7% over a period of about 40 days.

10. The liquid reagent set according to claim 1, wherein the reagent set further comprises a preservative.

11. The liquid reagent set according to claim 8, wherein the substituents of the hydrogen donor are defined as follows: $R_1$ is methyl; $R_2$ and $R_3$ are hydrogen; $R_4$ is $SO_3M$, wherein M is Na; and $R_5$ is methyl.

12. The liquid reagent set according to claim 10, wherein the preservative is sodium azide.

13. The liquid reagent set according to claim 12, wherein the substituents of the hydrogen donor are defined as follows: $R_1$ is methyl; $R_2$ and $R_3$ are hydrogen; $R_4$ is $SO_3M$, wherein M is Na; and $R_5$ is methyl.

14. The reagent set according to claim 13, wherein the buffer is a phosphate buffer.

15. The reagent set according to claim 14, wherein the reagent set exhibits a calibration factor that varies by less than about 7% over a period of about 40 days.

16. The reagent set according to claim 14, wherein the reagent set exhibits a calibration factor that varies by less than about 5% over a period of about 60 days.

17. A method for determining the concentration of L-lactate in a biological fluid, comprising the steps of:

a) collecting a biological fluid from a subject; and b) performing a spectrophotometric assay on the biological fluid using a liquid reagent set according to claim 1.

18. The method according to claim 17, wherein the hydrogen donor of the reagent set has substituents defined as follows: $R_1$ is methyl; $R_2$ and $R_3$ are hydrogen; $R_4$ is $SO_3M$, wherein M is a sodium ion; and $R_5$ is methyl.

19. A method for determining the concentration of L-lactate in a biological fluid, comprising the steps of:

a) collecting a biological fluid from a subject; and b) performing a spectrophotometric assay on the biological fluid using a liquid reagent set according to claim 9.

20. The method according to claim 19, wherein the hydrogen donor of the reagent set has substituents defined as follows: $R_1$ is methyl; $R_2$ and $R_3$ are hydrogen; $R_4$ is $SO_3M$, wherein M is a sodium ion; and $R_5$ is methyl.

* * * * *